(12) United States Patent
Wadekar et al.

US011773347B2

(10) Patent No.: US 11,773,347 B2
(45) Date of Patent: Oct. 3, 2023

(54) PREPARATION AND USE OF HIGH QUALITY ESTERQUATS FROM RICE BRAN FATTY ACIDS

(71) Applicant: Clariant International Ltd., Muttenz (CH)

(72) Inventors: Sushant Dattaram Wadekar, Pune (IN); Prerak Rajendrakumar Contractor, Singapore (SG)

(73) Assignee: CLARIANT INTERNATIONAL LTD, Muttenz (CH)

( * ) Notice: Subject to any disclaimer, the term of this patent is extended or adjusted under 35 U.S.C. 154(b) by 0 days.

(21) Appl. No.: 17/258,952

(22) PCT Filed: Jul. 10, 2019

(86) PCT No.: PCT/EP2019/068589
§ 371 (c)(1),
(2) Date: Jan. 8, 2021

(87) PCT Pub. No.: WO2020/011876
PCT Pub. Date: Jan. 16, 2020

(65) Prior Publication Data
US 2021/0284932 A1 Sep. 16, 2021

(30) Foreign Application Priority Data
Jul. 11, 2018 (EP) .................................. 18182944

(51) Int. Cl.
*C11D 1/62* (2006.01)
*C11D 3/00* (2006.01)
*C07C 227/28* (2006.01)
*C07C 229/22* (2006.01)

(52) U.S. Cl.
CPC .......... *C11D 3/0015* (2013.01); *C07C 227/28* (2013.01); *C07C 229/22* (2013.01); *C11D 1/62* (2013.01)

(58) Field of Classification Search
CPC ......... C11D 1/62; C11D 3/0015; C11D 1/645; C11D 3/2093; C07C 227/28
See application file for complete search history.

(56) References Cited

U.S. PATENT DOCUMENTS

| | | | |
|---|---|---|---|
| 5,811,385 A | 9/1998 | Eyrisch | |
| 5,830,845 A | 11/1998 | Trinh | |
| 6,072,063 A | 6/2000 | Eyrisch | |
| 8,802,876 B2* | 8/2014 | Darbha | C11B 13/00 554/160 |
| 2006/0094890 A1* | 5/2006 | Sharma | C11C 3/003 554/174 |
| 2009/0286712 A1 | 11/2009 | Gallotti | |
| 2012/0215017 A1* | 8/2012 | Darbha | C11C 1/06 554/160 |
| 2013/0196894 A1 | 8/2013 | Parrish | |
| 2016/0102273 A1 | 4/2016 | Declercq | |
| 2017/0275560 A1 | 9/2017 | Inoue | |

FOREIGN PATENT DOCUMENTS

| | | |
|---|---|---|
| CN | 1237199 | 12/1999 |
| CN | 1259934 | 7/2000 |
| CN | 1263552 | 8/2000 |
| CN | 103429747 | 12/2013 |
| CN | 106867660 | 6/2017 |
| DE | 10019142 | 10/2001 |
| EP | 0687291 | 12/1995 |
| EP | 0981512 | 3/2000 |
| EP | 1806392 | 7/2007 |
| EP | 2453001 | 5/2012 |
| JP | 2003252838 | 9/2003 |
| JP | 2003277334 | 10/2003 |
| WO | 9847991 | 10/1998 |
| WO | 9852907 | 11/1998 |
| WO | 2011018802 | 2/2011 |
| WO | 2014069833 | 5/2014 |
| WO | 2020011876 | 1/2020 |

OTHER PUBLICATIONS

Written Opinion, PCT/EP2019/068589, dated Jan. 12, 2019 (Year: 2019).*
Gunjan and Vinod K. Tyagi; "Synthesis of Rice Bran Fatty Acids (RBFAs) Based Cationic Surfactants and Evaluation of Their Performance Properties in Combination with Nonionic Surfactant", Tenside Surfactants Detergents, 51, 6, 497-505, Gunjan and Vinod K. Tyagi; "Synthesis of Rice Bran Fatty Acids (RBFAs) Based Cationic Surfactants and Evaluation of Their Performance Properties in Combination with Nonionic Surfactant", Tenside Surfactants Detergents, 51, 6, 497-505, URL: https://www.hanser-elibrary.com/doi/pdf/10.3139/113.110334 (Dec. 6, 2018).
International Preliminary Report on Patentability and Written Opinion for PCT/EP2019/068589, dated Jan. 12, 2021, 8 pages.
International Search Report for PCT/EP2019/068589, dated Sep. 24, 2019, 3 pages.
Murphy Dennis S: "Fabric Softener Technology: A Review", Journal of Surfactants and Detergents, Springer, Berlin, DE, vol. 18, No. 2, Dec. 10, 2014 (Dec. 10, 2014), pp. 199-204, XP035452301, ISSN: 1097-3958, DOI: 10.1007/ S11743-014-1658-2 [retrieved on Dec. 10, 2014] p. 201, right-hand column, paragraph 2.

(Continued)

*Primary Examiner* — Charles I Boyer
(74) *Attorney, Agent, or Firm* — Natali Richter

(57) ABSTRACT

Esterquats find major applications as fabric softeners. After Tallow fatty acids and Palm oil fatty acids, fatty acids from sustainable sources like Rice bran fatty acids (RBFA) are desired. RBFA is formed as a by-product during refining of Rice bran oil and hence it is contained in the non edible portion of the oil. The production of high quality esterquats from this by-product is challenging, but the invention describes a process to produce high quality esterquats having low odour and a low acid value. This enhances easy formulation of various products and better customer acceptance. Liquid esterquats produced from RBFA enable e.g. cold processing for fabric softener formulations.

17 Claims, No Drawings

(56) References Cited

OTHER PUBLICATIONS

Shi Can et al.: "Composition of Rice Bran Stearin from Various Refineries Across China", Journal of the American Oil Chemists Society, Springer, DE, vol. 93, No. 6, Apr. 27, 2016 (Apr. 24, 2016), pp. 869-877, XP035947599, ISSN: 0003-021X, DOI: 10.1007/S11746-016-2814-9 [retrieved on Apr. 27, 2016] p. 869, left-hand column, paragraph 1 p. 871, right-hand column, paragraph 3.

* cited by examiner

PREPARATION AND USE OF HIGH QUALITY ESTERQUATS FROM RICE BRAN FATTY ACIDS

The invention relates to the preparation and use of so called high quality esterquats from rice bran fatty acids derived from a non-edible source. Esterquats are a class of cationic surfactants mainly used in laundry applications such as fabric softeners. Esterquats generally contain a long chain fatty acid group linked to a quaternary ammonium group via ester linkage. The structure and composition of esterquats are described e.g. in EP-A 1806392. Esterquats are generally prepared by using triethanolamine esterified with long chain fatty acids (e.g. C16-C18), followed by quaternisation with a suitable quaternising agent, such as dimethyl sulphate. Other types of esterquat structures, such as mentioned in U.S. Pat. Nos. 6,072,063 and 5,811,385, are also known. In general, esterquats can also be prepared directly from triglyceride oils via a trans-esterification step followed by a quaternisation step as described e.g. in WO 2014/069833.

The quality of esterquat products is defined by their activity, acid value, odour and colour, which are parameters affecting both product performance and customer acceptance. So called high quality esterquat products can be obtained by selecting proper parameters during the manufacturing process of the esterquats. For example, it was found that having a low acid value esterquat results in an esterquat composition having higher viscosity as compared to an esterquat having a high acid value. From a product performance perspective, a higher viscosity formulation is perceived as being more stable and aesthetically more appealing to consumers.

EP-A 0981512 describes the use of a typical process to achieve acid values <6.5 mg KOH/g. US 2009/286712 describes esterquats with low acid values (<6.7 mg KOH/g) but for esterquats synthesised using methyl-diethanolamine. The applications JP 2003277334 A and JP 2003252838 A describe a process wherein no solvent is used during the quaternisation step, which leads to a better quality of the product. US 2017/275560 describes the use of an oxidising agent to achieve a light coloured esterquat product.

Cold processability of esterquats and/or dispersibility of esterquats at low temperatures are further desired properties of the high quality products due to better energy economy and production convenience.

US 2013/196894 describes an esterquat composition product synthesised using fatty acids having an iodine value between 65-85 and a good ester distribution for promoting dispersibility at low temperatures.

Esterquats are generally prepared by using fatty acids based on tallow or vegetable oils such as palm oil. However, there are also other types of vegetable oils that have been reported, including sunflower, soybean and rice bran oil. However a renewable, non-edible (in particular for humans) and sustainable source for esterquats is highly desirable.

Fatty acid esterquats, for example based on palm oil fatty acids, and the use thereof in compositions for various uses, in particular as cationic surfactant in laundry products, are known since more than 20 years (see e.g. U.S. Pat. No. 5,830,845). The use of rice bran fatty acid (RBFA) esterquats as cationic surfactants in fabric softeners has been reported in the publication Gunjan and Vinod K. Tyagi (2014) ("Synthesis of Rice Bran Fatty Acids (RBFAs) Based Cationic Surfactants and Evaluation of Their Performance Properties in Combination with Nonionic Surfactant", Tenside Surfactants Detergents: Vol. 51, No. 6, pp. 497-505). It is described that RBFA esterquats can be prepared by esterification of RBFA with hydroxyalkylamines, such as diethanolamine (DEA) or triethanolamine (TEA) at 140° C. for 3 to 4 hours, and following "quaternisation" of the obtained di-ester using dimethylsulphate (DMS). The publication also describes dilute esterquat products prepared using hydrolysed fatty acids from rice bran oil. Even though rice bran oil is a by-product of rice bran processing, the cost of rice bran oil is high and the oil is categorized as an edible product. Therefore, the use of rice bran oil for the manufacture of esterquats is undesirable.

However there are other sources of RBFA that do not fall under the edible category. During extraction of rice bran oil, a substantial amount of oil undergoes degradation due to enzymatic activity, forming fatty acids in the non-edible crude rice bran oil. To make this oil edible, this oil is refined by separating the fatty acids by alkali refining or steam distillation. The resultant rice bran fatty acids generated as the by-product of rice bran oil are components of a non-edible portion of the oil and hence are more favourable for the production of products unrelated to food. Thus, food-grade oil would not be wasted for non-food purposes and the rice bran would be utilised to the fullest. However, being a by-product, RBFA from non-edible sources usually contain impurities, thus making the production of high quality esterquats from these sources challenging.

In the present invention, a non-edible source of RBFA has been used for the synthesis of high quality esterquat composition products by using appropriate process parameters. The fatty acid compositions of this esterquat composition product can be changed via various separation techniques like crystallisation, winterisation (i.e. sweating) or distillation. Depending on the composition of fatty acids, the esterquat product can be solid or liquid. In case of liquid RBFA-based esterquat composition products, cold processing is enabled.

Rice bran fatty acids (RBFA) are a sustainable resource produced in rice bran processing. A substantial amount of fatty acids are formed due to enzyme action during the processing of rice bran. These fatty acids are components of the non-edible portion of crude rice bran oil and have to be separated from the oil to make the edible food-grade oil. These RBFA from the non-edible source have been tested according to the invention as raw material for the synthesis of esterquats.

The abbreviation RBFA and the term "rice bran fatty acids" refer here to rice bran fatty acids which stem from a non-edible source, unless stated otherwise.

The basic chemistry involved in the synthesis of esterquats using RBFA corresponds with the prior art involving palm oil fatty acids. However, since RBFA is generated as a by-product and thus contains impurities, the quality of esterquats synthesized using RBFA can be lower, if a proper process is not used.

A new specific synthesis process for the preparation of esterquat composition products is described, using rice bran fatty acids from non-edible sources, which results in the high quality of the products, the high quality esterquats.

One normal way of production of esterquats is carrying out quaternisation with dimethyl sulphate in the presence of a solvent to avoid formation of a non-stirrable highly viscous reaction slurry. However, the use of solvents in this step was found to lead to the formation of unpleasant odour causing compounds, acidic by-products and colour stain of the product, and thus reduce the quality of the esterquat composition product.

In another process solvent is added after the quaternisation is complete, thereby minimizing the formation of odour causing materials and acidic by-products. In the present invention, this process is extended to RBFA. This results in a high quality esterquat composition product with reduced odour, acidity and colour stain. All these quality parameters enhance an easy formulation of final products and customer acceptance.

In particular, the present invention provides a process for the production of an esterquat composition product comprising the steps of:

(i) esterification of a fatty acid or a mixture of fatty acids with an alkanolamine to form an ester amine or a mixture of ester amines; and (ii) quaternisation of the amino group of the resultant ester amine or the amino groups of the mixture of ester amines with a quaternising agent, preferably dimethyl sulphate, wherein the fatty acid or mixture of fatty acids is based on a rice bran fatty acid or a mixture of rice bran fatty acids from non-edible sources generated during refinement of rice bran oil.

Furthermore, an object of the present invention is a high quality esterquat composition product prepared by the described process, as well as a fabric softener composition comprising the high quality esterquat composition product.

Moreover, the use of a rice bran fatty acid or a mixture of rice bran fatty acids from non-edible sources generated during refinement of rice bran oil for the production of an esterquat composition product is provided.

In the process according to the invention, the esterification step (i) is typically carried out at temperatures between 50 and 250° C., preferably between 100 and 200° C., more preferably between 130 and 180° C. If the temperature is too low, the reaction is significantly slowed down and thus is not applicable on an industrial scale. However, if the temperature is too high, decomposition products occur at a high rate, thus limiting the usefulness of the product mixture.

Preferably, the esterification step (i) is carried out under conditions in which generated water is continuously removed from the reaction vessel. For example, water removal may be accomplished by adding molecular sieves to the reaction mixture, by attaching a Dean-Stark-apparatus or distillation apparatus to the reaction vessel, or by applying vacuum to the reaction vessel. Preferably, the reaction is carried out under vacuum or with a distillation apparatus attached.

The alkanolamine used in the process according to the invention may be any alkanolamine, however tertiary alkanolamines are preferred. Even more preferred are trialkanolamines, especially triethanolamine.

The rice bran oil, from the refinement of which the non-edible source of rice bran fatty acids is generated, is not particularly limited. It is, however, desirable to select rice bran oil that is a side product of rice bran processing. The rice bran itself is also not limited to specific rice bran, but is preferably rice bran that is a by-product of rice processing.

The rice bran fatty acids from non-edible sources are usually obtained as a mixture of several fatty acids and often contain impurities that prevent the formation of high quality esterquat composition products using conventional processes. Therefore the rice bran fatty acids may be separated and/or chemically processed before they are subjected to the esterification step (i).

Chemical processing may include any chemical processing steps typically used for processing fatty acids, however chemical processes for saturating unsaturated bonds are preferred. Exemplary means of chemical processing of RBFA are halogenation, hydrohalogenation, hydroboration, ozonolysis, Diels-Alder reactions, hydrogenation, and epoxidation. Preferred means of chemical processing of the rice bran fatty acids from the non-edible source are epoxidation and catalytic hydrogenation.

Separation techniques for rice bran fatty acids may include any known separation techniques that are applicable for the separation of fatty acids from each other and/or from further impurities. These separation techniques include, but are not limited to crystallisation, winterisation, distillation, sublimation, filtration, chromatography including column, flash, and high performance liquid chromatography, liquid-liquid extraction and solid-liquid-extraction. Preferable separation techniques are crystallisation, winterisation and/or distillation.

The molar ratio of rice bran fatty acids to alkanolamine in the esterification step (i) is typically from 1:2 to 3:1, preferably 1:1 to 3:1, more preferably from 1:1 to 2:1. If the ratio is too low, the resultant ester amines are formed in an undesirably low concentration. However, if it is too high, the resultant product exceeds the desired acidity. Accordingly, depending on the ratio and the employed alkanolamine, the resultant ester amine or mixture of ester amines may contain monoesters, diesters, triesters or mixtures thereof.

The quaternisation step (ii) is typically carried out at temperatures from 0 to 180° C., preferably from 20 to 120° C., more preferably from 50 to 100° C. If the temperature is too low, the reaction is significantly slowed down and thus is not applicable on an industrial scale. However, if the temperature is too high, decomposition products occur at a higher rate and undesired methylation of the other functional groups may take place.

The quaternising agent in the quaternization step (ii) is not particularly limited and may be selected, e.g. from trialkyl oxonium salts, alkyl halides, dialkyl phosphates, dialkyl carbonates, alkyl sulphonates and dialkyl sulphates, however dialkyl sulphates are preferred, especially dimethyl sulphate.

In the quaternization step (ii) the molar ratio between the ester amine and the quaternising agent is typically from 2:1 to 1:3, preferably from 1.5:1 to 1:2, most preferably from 1.1:1 to 1:1.1. If the ratio is too low, the quaternisation of the ester amine or the mixture of ester amines is not complete after the reaction is finished. If the ratio is too high, there is a risk that other functional groups of the product are alkylated.

Preferably, at least a part of the quaternisation step (ii), more preferably the full quaternization step (ii) is carried out in the absence of a solvent, because solvents may be alkylated by the quaternizing agent, which may result in increased odour of the final product. However, one or more solvents may be added to the resultant mixture after the quaternization is at least partially completed, preferably fully completed. The solvent is not particularly limited, and can be selected from, e.g. lower alcohols having from 1 to 6 carbon atoms such as ethyl alcohol, propyl alcohol, isopropyl alcohol, etc; polyols, such as ethylene glycol, diethylene glycol, propylene glycol, polyethylene glycol and glycerin, and they can be used alone or in a combination thereof. Preferably the solvent added after the at least partial completion of the quaternization step is an alcohol. Most preferably, the alcohol is ethanol or isopropanol.

The solvent may comprise further solvent components, such as aromatic hydrocarbons, aliphatic hydrocarbons, ethers, esters, lactones, lactams, amides, amines, furans and others. Preferably the solvent does not contain any of these further solvent components.

The process according to the present invention leads to an esterquat composition product that has high quality. The esterquat composition product has a low acid value, a low level of odour and a low level of coloured stain.

The acid value of the esterquat composition product prepared by the process according to the invention is typically lower than 7 mg KOH/g of the sample, and usually originates from the content of amine salts and free fatty acids in the product. The acid value may be determined by the recent standard method ASTM D 974.

The odour of the esterquat composition product mostly originates from the solvent employed in or after the quaternisation step (ii), which solvent is often alkylated by the quaternising agent to give compounds with unpleasant odour. The esterquat composition product acquired by the process of the invention typically contains alkylated solvents, preferably alkylated alcohols, in particular methyl ethyl ether or methyl isopropyl ether in an amount below 10000 ppm, preferably below 5000 ppm, more preferably below 2000 ppm, as determined by integration of the corresponding resonance signals, preferably of the signals arising from the methyl groups introduced by the quaternising agent, in the $^1$H NMR spectrum of a sample of the esterquat composition product.

The colour of the esterquat composition product acquired by the process according to the invention typically has a value of less than 8, preferably less than 5, more preferably 4 or less on the Gardner colour scale according to the recent standard method ASTM D1544.

The esterquat composition product acquired by the process according to the invention preferably has an active esterquat content of above 0.7 meq/g, more preferably of above 0.8 meq/g, most preferably of above 1.0 meq/g, measured by Epton titration.

The esterquat composition product acquired by the process according to the invention can be mixed with further ingredients to form a fabric softener composition. These further ingredients are not particularly limited and may be any ingredients typically used in fabric softener compositions. These ingredients may be optionally included in the composition of the present invention to provide additional functions. Specifically, an organic solvent, preferably selected from the group consisting of isopropanol, ethanol, benzyl alcohol, glycerin, propylene glycol and mixtures thereof may be added for further stabilizing the fabric softener composition;

acids or bases may be included for maintaining the optimal pH for further stabilization of the composition. Further examples of optional ingredients include, but are not limited to builders, surfactants, bleaching agents, bleach active compounds, bleach activators, bleach catalysts, photo-bleaches, dye transfer inhibitors, colour protection agents, anti-redeposition agents, dispersing agents, antistatic agents, fluorescent whitening agents, enzymes, enzyme stabilizing agents, foam regulators, defoamers, odour reducers, preservatives, disinfecting agents, hydrotopes, fibre lubricants, anti-shrinkage agents, buffers, fragrances, processing aids, colourants, dyes, pigments, anti-corrosion agents, fillers, stabilizers and other conventional ingredients for fabric softener compositions. The amount of esterquat composition product in the fabric softener composition is preferably 20 to 90 wt-%, more preferably 30-80 wt.-%.

In the following examples and claims, the invention is disclosed in more detail.

COMPARATIVE EXAMPLE 1

900 g of rice bran oil (1 mole) was heated with 150 g of caustic lye (32%) solution at 70° C. for 2 hours to accomplish saponification. The soap formed was carefully extracted three times (each time with 500 ml) with n-hexane to remove unsaponified oil. The soap was further acidulated with 500 ml of 15% $H_2SO_4$.

The organic layer was further washed three times with 500 ml of water and then dried under vacuum. A portion of the resulting rice bran fatty acids (100 g, 0.35 moles) were reacted with triethanolamine (26.3 g, 0.176 moles) using the catalyst hypophosphoric acid (25 ppm) at 140° C. and 10 mm Hg pressure for 4 hours to form ester amine. The intermediate was cooled to room temperature. The acid value of the intermediate was measured using ASTM D 974 test method and was found to be 5.1 mg KOH per gram of sample. The required quantity (68 g, 0.1 moles) of the ester amine was dissolved in 200 ml of isopropanol. Dimethyl sulphate (12.6 g, 0.1 mole) was added and the mixture was heated at 60° C. for 16 hours to allow all the DMS to react. A dark brown coloured product was obtained having the properties as shown in Table 1. Low active content of Comparative Example 1 as compared to Example 1 is due to presence of excess solvent employed during the production process.

EXAMPLE 1

100 g (0.35 moles) of rice bran fatty acid obtained as a by-product from rice bran oil processing, was reacted with triethanolamine (34.8 g, 0.234 moles) using the catalyst hypophosphoric acid (25 ppm) at 180° C. for 6 hours under atmospheric pressure while water was continuously removed by distillation. The intermediate (i.e. ester amine) was cooled to room temperature and had an acid value of 2.4 mg KOH/g.

110 g (0.2 moles) of the ester amine was heated to 80° C. and 24.1 g (0.191 moles) of DMS was added over the period of 105 minutes, and the reaction was continued for additional 10 minutes to allow DMS to react. The development of a highly viscous mass indicated the reaction with DMS. Thereafter, 14.9 g of ethanol were added continuously over the period of 80 minutes and the reaction was continued for next two hours at 80° C. Light yellow coloured product was obtained (Table 1). As compared to Comparative Example 1, the inventive sample thus prepared was markedly different exhibiting low colour and low acid value, which shows the high quality and is desirable for further processing to form e.g. laundry compositions.

TABLE 1

| Analysis of Esterquat products | | |
|---|---|---|
| | Comparative Example 1 | Example 1 |
| Acid value (mg KOH/g) | 31.6 | 6.6 |
| Colour (Gardner colour scale) | 12.9 | 4.0 |
| Active content (Epton, meq/g) | 0.50 | 1.04 |

With the high quality esterquat of Example 1, having a low colour and a low acid value, a fabric softener compositions can be advantageously be prepared by simple and common process steps.

The invention claimed is:
1. A process for production of an esterquat composition, wherein the process comprises the steps of:
   (i) esterification of a fatty acid or a mixture of fatty acids with an alkanolamine to form an ester amine or a mixture of ester amines; and

(ii) quaternization of the amino group of the resultant ester amine or the amino groups of the mixture of ester amines with a quaternizing agent, wherein the fatty acid or mixture of fatty acids is a rice bran fatty acid or a mixture of rice bran fatty acids, and are from non-edible sources generated during refinement of a rice bran oil, and wherein the fatty acid or mixture of fatty acids is directly esterified, is subjected to a chemical processing before being esterified, is changed before being esterified by using one or more separation techniques, or a combination thereof.

2. The process according to claim 1, wherein the alkanolamine in the esterification step (i) is a trialkanolamine.

3. The process according to claim 1, wherein at least a part of the quaternization step (ii), is carried out without a solvent, and a solvent is optionally added only after the at least partial completion, of the quaternization step (ii).

4. The process according to claim 1, wherein a solvent is used after the quaternization step (ii) and the solvent is an alcohol.

5. The process according to claim 1, wherein the crude rice bran oil, is a side product of rice bran processing.

6. The process according to claim 1, wherein the rice bran fatty acid or mixture of rice bran fatty acids is subjected to a step of chemical processing before the esterification step (i), wherein the step of chemical processing is selected from the group consisting of halogenation, hydrohalogenation, hydroboration, ozonolysis, Diels-Alder reactions, hydrogenation, epoxidation and any combination thereof.

7. The process according to claim 1, wherein the composition of rice bran fatty acids or mixture of rice bran fatty acids is changed before the esterification step (i) by using one or more separation techniques selected from the group consisting of crystallisation, winterisation, distillation, sublimation, filtration, chromatography including column, flash, high performance liquid chromatography, liquid-liquid extraction, solid-liquid-extraction and any combination thereof.

8. The process according to claim 1, wherein the esterification step (i) is carried out at temperatures between 50 and 250° C. and/or the quaternisation step is carried out at temperatures from 20 to 120° C.

9. The process according to claim 1, wherein the molar ratio of fatty acids to alkanolamine in esterification step (i) is from 1:2 to 3:1.

10. The process according to claim 1, wherein the molar ratio of ester amine to quaternising agent in the quaternisation step (ii) is from 2:1 to 1:3.

11. An esterquat composition product prepared by a process according to claim 1.

12. The esterquat composition produced by the process according to claim 1, wherein the acid value of the esterquat composition is lower than 7 mg KOH/g of the sample.

13. The esterquat composition produced by the process according to claim 1, wherein the esterquat composition has an active esterquat content of above 0.7 meq/g as measured by Epton titration.

14. The esterquat composition produced by the process according to claim 1, wherein the content of a methylated solvent is below 10000 ppm.

15. The esterquat composition produced by the process according to claim 1, having a colour value on the Gardner colour scale of less than 8.

16. The esterquat composition produced by the process according to claim 1, wherein the esterquat composition is a liquid esterquat composition.

17. A fabric softener composition comprising the esterquat composition product according to claim 11.

* * * * *